US009700739B2

(12) United States Patent
Martin et al.

(10) Patent No.: US 9,700,739 B2
(45) Date of Patent: *Jul. 11, 2017

(54) SYSTEM AND COMPUTER PROGRAM PRODUCT FOR INVERSE TREATMENT PLANNING

(71) Applicant: Intuitive Therapeutics SA, Sion (CH)

(72) Inventors: Andre Martin, Preverenges (CH); Daniel Salzmann, Saint Prex (CH)

(73) Assignee: Intuitive Therapeutics SA (CH)

( * ) Notice: Subject to any disclaimer, the term of this patent is extended or adjusted under 35 U.S.C. 154(b) by 48 days.

This patent is subject to a terminal disclaimer.

(21) Appl. No.: 14/317,194

(22) Filed: Jun. 27, 2014

(65) Prior Publication Data

US 2015/0360051 A1    Dec. 17, 2015

(30) Foreign Application Priority Data

Jun. 17, 2014    (CH) ..................................... 0914/14
Jun. 17, 2014    (CH) ..................................... 0915/14

(51) Int. Cl.
*A61B 6/00*    (2006.01)
*A61N 5/10*    (2006.01)
(Continued)

(52) U.S. Cl.
CPC ........... *A61N 5/1031* (2013.01); *A61N 5/103* (2013.01); *A61N 5/1075* (2013.01);
(Continued)

(58) Field of Classification Search
CPC .... A61N 5/1031; A61N 5/103; A61N 5/1049; A61N 5/1042; A61N 5/1039;
(Continued)

(56) References Cited

U.S. PATENT DOCUMENTS

2006/0274885 A1*  12/2006  Wang ................... G06Q 50/22
                                                            378/65
2006/0274925 A1*  12/2006  West ..................... A61N 5/103
                                                            382/131
(Continued)

FOREIGN PATENT DOCUMENTS

WO    WO-2009137010 A2    11/2009

*Primary Examiner* — Anastasia Midkiff
(74) *Attorney, Agent, or Firm* — Blank Rome LLP

(57) ABSTRACT

The present invention concerns an inverse treatment planning system. The system includes, at least a data bus system (102), a memory (106) coupled to the data bus system (102), and a processing unit (104) coupled to the data bus system (102). The processing unit (104) is configured to execute the instructions to pre-compute (10) a set of individual dose shots ($a^j$), each individual dose shot having a predetermined location inside and/or outside a target area, a size and a shape. The processing unit also associates (40) a weight ($s_j$) to each individual dose shot ($a^j$), based on one or more constraints (20). The processing unit (104) further executes the instructions to find (30) the sparsest subset of individual dose shots, so as to satisfy said one or more constraints (20).

18 Claims, 2 Drawing Sheets

(51) Int. Cl.
*G06F 17/16* (2006.01)
*G01T 1/29* (2006.01)
*G06F 17/30* (2006.01)

(52) U.S. Cl.
CPC ...... *G06F 17/30271* (2013.01); *A61B 6/5294* (2013.01); *A61B 6/54* (2013.01); *A61N 5/1038* (2013.01); *A61N 5/1042* (2013.01); *A61N 5/1047* (2013.01); *A61N 5/1071* (2013.01); *G01T 1/2914* (2013.01); *G05B 2219/33079* (2013.01); *G06F 17/16* (2013.01)

(58) Field of Classification Search
CPC .......... A61N 2005/1087; A61N 5/1037; A61N 5/1047; A61N 5/10; A61N 5/1045; A61N 5/1067; A61N 5/1081; A61N 2005/1041; A61N 2005/1055; A61N 5/1077; A61N 5/1064; A61N 5/00; A61N 5/1038; A61N 5/1071; A61N 5/1075; A61N 2005/0626–2005/0628; A61B 6/00; A61B 6/52; A61B 6/5205; A61B 6/5211; A61B 6/5294; A61B 6/54; G05B 2219/34017; G05B 2219/33079; G06F 7/52; G06F 7/78; G06F 9/00; G06F 9/30; G06F 9/30003; G06F 9/30007; G06F 9/30036; G06F 15/8053; G06F 15/76; G06F 15/80; G06F 17/00; G06F 17/10; G06F 17/16; G06F 17/30244; G06F 17/30271; G01T 1/1663; G01T 1/2992; G01T 1/2914; G01T 1/29; G01T 1/2928; G01T 1/2964; G01T 1/2971; G01T 1/2978; G01T 1/2985
USPC .................................................. 378/4, 9, 65
See application file for complete search history.

(56) References Cited

U.S. PATENT DOCUMENTS

2013/0188856 A1    7/2013   Adler, Jr. et al.
2013/0346082 A1* 12/2013   Aly .................. G06F 17/30943
                                                                                 704/270

* cited by examiner

SYSTEM AND COMPUTER PROGRAM PRODUCT FOR INVERSE TREATMENT PLANNING

REFERENCE DATA

The present application claims the priority of Swiss Patent Application CH0914/14, filed on Jun. 17, 2014, the content of which is incorporated here by reference, and of the of Swiss Patent Application CH0915/14, filed on Jun. 17, 2014, the content of which is incorporated here by reference.

FIELD OF THE INVENTION

The present invention relates to therapy and surgery, e.g. to radiation therapy and surgery. In particular, the present invention concerns a system and a computer program product for inverse treatment planning.

DESCRIPTION OF RELATED ART

Radiation therapy and radiation surgery (or radiosurgery) are therapeutic approaches, which are efficient, non-invasive and compatible with outpatient treatments.

In the context of radiosurgery, and in particular in brain neurosurgery, a tool commonly used for treating intracranial diseases is commercialised under the name "Leksell Gamma Knife®" or simply "Gamma Knife®".

Leksell Gamma Knife® utilizes concomitant gamma rays from multiple Cobalt-60 radiation sources focused at an isocentre, and a stereotactic frame that serves as a coordinate system and immobilization device. Recently, Leksell Gamma Knife® has also been equipped with image-guided frameless immobilization devices.

The treatment is performed by localizing the patient's disease brain region, the so-called target region, with a medical imaging study and positioning the target region at the focused intersection of the beams (i.e. the isocentre).

The treatment can be realized in one shot, i.e. by positioning one single part or location of the target region at the isocentre. It can also be realized using multiple shots, i.e. by successively placing different parts of the target area at the isocentre.

In the context of the present invention, a shot (or dose shot) is then a dose, e.g. a radiation dose. It is characterized by a location (i.e. the location of the centre of the shot), a size and a shape. Thanks to the use of different collimators and the blocking or not of some of the beams, Leksell Gamma Knife® can provide shots having different sizes and shapes.

For each shot, the user has to determine its location in the target area, as well as the size and shape of the irradiation dose to be delivered around the isocentre, specifying respectively the collimators to be used and the beams of Leksell Gamma Knife® to be blocked or not.

For each shot, the user has also to determine the time of irradiation, parameterized by the so-called weight of the shot, in relation of the dose-rate of the radioactive cobalt sources.

Leksell Gamma Knife® radiosurgery consists of a planning phase and a delivery phase. In the planning phase, each patient's treatment plan is developed by a neurosurgeon working in conjunction with a radiation oncologist and a physicist. According to the most widely used planning procedure, they determine, through an iterative process of trial and error, the number and location of shots, along with their size, shape, and weight. When the treatment volume is small, the treatment plan may only require one or two shots. The planning process, however, becomes more complex for both irregularly shaped and larger-size target regions. For these cases, the complexity of the treatment planning process makes it difficult to take full advantage of the powerful capabilities of Leksell Gamma Knife®. This is especially true in the latest version, Leksell Gamma Knife® Perfexion™, where the cobalt sources are grouped in sectors that align concomitantly with collimators of the same size. Each individual sector can be align with specific collimators size (composite shot) or can be blocked.

Gamma Knife® radiosurgery requires thus a critical stage of planning, in order to create the optimal dosimetry, based on the location and dose to be delivered to the target to be irradiated, and to those to be protected from a too strong irradiation.

This dosimetry, as discussed, is based on the use of one or more irradiation isocentres (i.e. the focal points of convergence of the rays of the Gamma Knife). The technical parameters to be set for creating a dose distribution adapted to the desired irradiation of the target are mainly:
- the number of the irradiation focal points (isocentres),
- the location of the isocentres,
- the size and shape of the collimation of the irradiation beams (including the possibility to create composite shots with Leksell Gamma Knife® Perfexion™)
- the weight of the different irradiation isocenters.

These technical parameters must take into account the choice of a specific dose and isodose prescription. The current procedure for the planning step is relatively complex, tedious, unintuitive and slow. The duration of the planning procedure decreases the productivity and increases the cost of every treatment. Moreover its quality depends essentially on the experience of the user. Acquiring this experience requires a long training period in one of the few reference centres in the World.

Indeed, the current way to do the planning requires, as described above, to define technical parameters of the machine that will ultimately produce the desired dose distribution. The relationship between those parameters and the actual dose distribution is not always intuitive. The user is thus asked to acquire and exploit a technical expertise, while he/she should rather concentrate on the medical aspects of the treatment.

To help the user, automatic inverse planning systems have been proposed. The planning is "inverse" as, based on the knowledge of the target region properties (e.g. from CT or MRT images), the operator prescribes a certain dose distribution within the target region and/or certain dose constraints. An automatic inverse planning system finds a set of parameters resulting in a treatment planning which is as close as possible to the predetermined dose distribution.

The classic inverse planning procedure requires then the definition, by the operator, of the target area and the minimum dose that should be delivered to it. Secondarily, the planning system also helps to minimize the dose to the areas to be protected.

The inverse planning is then typically defined as an optimization problem where the technical parameters are automatically searched to minimize a cost function measuring the difference between the desired dose distribution and that actually achieved. Various optimization techniques may be used.

Currently, this solution is rarely used in clinical practice, and is difficult to understand for new users. Moreover, it may require further manual planning adjustments by the user, but he/she does not exploit its full potential, both because the user will not test a full range of technical parameters, and because he/she has time constraints during the planning procedure. The same remarks apply when fully manual planning is performed by the user.

WO2009137010 describes a system for developing a dynamic scheme for Gamma Knife® radiosurgery based on the concept of "dose-painting". The spherical high dose volume is viewed as a 3D spherical "paintbrush", and treatment planning is reduced to finding the best route of this "paintbrush" to "paint" a 3D target volume. Under the dose-painting concept, the patient is moving continuously under the robotic positioning system.

In this document, a large set of potential shots is computed and a shot selection can be performed in this set by using a constrained least square optimization algorithm. In particular the L2 norm of the difference between the created dose distribution and the ideal dose distribution is minimized subject to two constraints: the beam-on time for each shot must be higher than a threshold and the sum of the beam-on times of all shots (i.e. the final delivery time) must be less than or equal to the desired delivery time. By minimizing this difference, there is no guarantee that the minimal dose inside the target region is delivered at all points. Similar, there is no guarantee that a irradiation higher that the maximal dose allowed is not delivered to some points of predefined sensitive areas. Although theoretically appealing, the background and rationale of this system is not clear, and its clinical relevance remains to be proven.

US2013188856 concerns a system and method for real-time target validation for image-guided radiation therapy. This document describes how to validate in real-time that the predicted radiation dose is delivered to the actual target according to the planning. In particular, a displacement detection is performed to ascertain any displacement of the therapeutic radiation beam with respect to the target. A real-time feedback is then performed to correct the position of the beam in real-time should any displacement of the target be determined. The displacement of the target is evaluated by comparing stored images with live in-treatment images using a sparsity constraint on the measurements for acquiring live in-treatment images. The system for determining e.g. the real thickness of the skull is linear and solved by a convex optimization problem.

It is then an aim of the present invention to obviate or mitigate one or more of the aforementioned disadvantages.

It is an aim of the present invention to provide an inverse treatment planning system, which can simplify the planning phase of a treatment.

It is an aim of the present invention to provide an inverse treatment planning system, which is an alternative to the existing systems.

BRIEF SUMMARY OF THE INVENTION

According to the invention, these aims are achieved by means of an inverse treatment planning system, comprising:
  at least a data bus system,
  a memory coupled to the data bus system, wherein the memory comprises a computer usable program code, and
  a processing unit coupled to the data bus system, wherein the processing unit is configured to execute the computer usable program code to
    pre-compute a set of individual dose shots, each individual dose shot having a predetermined location inside and/or outside a target area, a size and a shape,
    associate a weight to each individual dose shot, based on one or several constraints.

The inverse treatment planning system of the present invention can be a focal inverse treatment planning system. In the context of the present invention, the expression "focal treatment" indicates focusing on a target, e.g. specific areas of an abnormal area (e.g. a tumor) of a patient, the source of this treatment being outside of the body of the patient (non-limitative examples of a focal treatment are the Gamma Knife® and the HIFUS, i.e. High-Intensity Focused Ultrasound).

The inverse treatment planning system of the present invention can be an internal local inverse treatment planning system. In this case, the source of this treatment is inside of the body of the patient. Brachytherapy, cryotherapy, radiofrequency ablation and intraoperative therapies are non-limitative examples of internal local treatments.

An inverse treatment planning system can be a system that does not use radiations. Cryotherapy and radiofrequency ablation are non-limitative examples of a treatment that does not use radiations.

A focal inverse treatment planning system can be a system that uses radiations: in this case, it can be a radiation inverse treatment planning system. Radiosurgery and radiotherapy are non-limitative examples of radiation treatments.

A radiation inverse treatment planning system can use ionizing radiations (as e.g. in the Gamma Knife®). In another embodiment, the focal inverse treatment planning system involves radiations different from ionizing radiations, e.g. non-ionizing radiations. High-intensity focused ultrasound is a non-limitative example of a focal treatment that does not use ionizing radiations.

The use of a sparsity criterion allows to eliminate a lot of solutions a priori not-possible, and then to quickly converge to a solution. The sparsity allows then computations in real-time, so that it is possible to perform a real-time calculation of the shots.

Advantageously the one or more constraints can be related to the corresponding resulting dose distribution.

Advantageously the weight may be representative of the time of irradiation of the single or individual dose shot.

The size and shape of the individual dose shots can be based on the size of collimators used for each sector, and their possible blocking.

In a preferred embodiment, the constraint comprises at least the coverage of the whole of part of the target region by a desired dose distribution. Further constraints may be added to modify the dose distribution outside of the target volume, and to limit the maximal dose to defined structures. Constraints may also be added to define the dose distribution within the target volume, if desired.

According to the invention, the processing unit executes the computer usable program code to
  find the sparsest subset of shots so as to satisfy the constraint(s).

The inventive system according to the invention allows to drastically simplify the radio-surgical planning via real-time inverse planning system.

In a preferred embodiment, the processing unit executes the computer usable program code to find the minimum number of non-zero weights so as to satisfy said one or more constraints.

The inventive system according to the invention allows to calculate the optimal technical parameters of irradiation to achieve the constraints imposed on the dose distribution. Considering the number of parameters that can be defined by the user during a manual planning, the optimal solution is in practice almost impossible to find, especially in the treatment of complex shape targets, even by an experienced user.

The inventive system according to the invention allows the user to interactively define the constraints on the dose to be delivered, in coverage, magnitude and gradients at the edges of the target or anywhere else in the volume of interest.

The advantages for the user are at least the following:

He/she does not have to concentrate on the technical aspect of the realization of the desired dose distribution, but only has to consider which dose he/she wants to administer, and where.

The interactive planning tool allows him/her to decide and modify in real-time the shape of the dose distribution to ensure proper irradiation of the target and proper protection of other organs.

The planning becomes intuitive, fast, and thus cost-effective.

The user can also easily add more constraints on the problem, such as a maximal treatment duration, the system providing the best possible planning to be as close as possible to the desired dose distribution while remaining within the time budget, for example.

The planning procedure performed by the system according to the invention is much more simple, faster and more user friendly than the known solutions, especially in complex target shapes Moreover the irradiation of multiple targets in a single procedure (e.g. brain metastases) with the system according to the invention becomes really practicable in a reasonable time.

The present invention concerns also a computer program product, comprising:
a tangible computer usable medium including computer usable program code for an inverse treatment planning, the computer usable program code being used for
   pre-compute a set of individual dose shots, each individual dose shot having a predetermined location inside and/or outside a target area, a size and a shape,
   associate a weight to each individual dose shot, based on one or more constraints, e.g. on the corresponding resulting dose distribution,
characterised in that the processing unit executes the computer usable program code to
   find the sparsest subset of individual dose shots, so as to satisfy said one or more constraints.

The present invention concerns also a computer data carrier storing presentation content created with an inverse treatment planning method, comprising the following steps:
   pre-compute a set of individual dose shots, each individual dose shot having a predetermined location inside and/or outside a target area, a size and a shape,
   associate a weight to each individual dose shot, based on one or several constraints, e.g. on the corresponding resulting dose distribution,
characterised in that the processing unit executes the computer usable program code to
   find the sparsest subset of individual dose shots, so as to satisfy said one or more constraints.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Although the present invention will be described in more detail in connection with Gamma Knife® radiosurgery, the application of which is exclusively cranial, the present invention finds applicability of connection with many other fields, as explained here above. For example, it can be applied also to extra-cranial radiosurgery techniques, or to treatments using any type of ionizing radiation, e.g. in fractionated radiotherapy techniques using linear accelerators (e.g. the Versa HD by Elekta). It can be applied also in robotic surgery or computer-assisted surgery.

Figure 1:
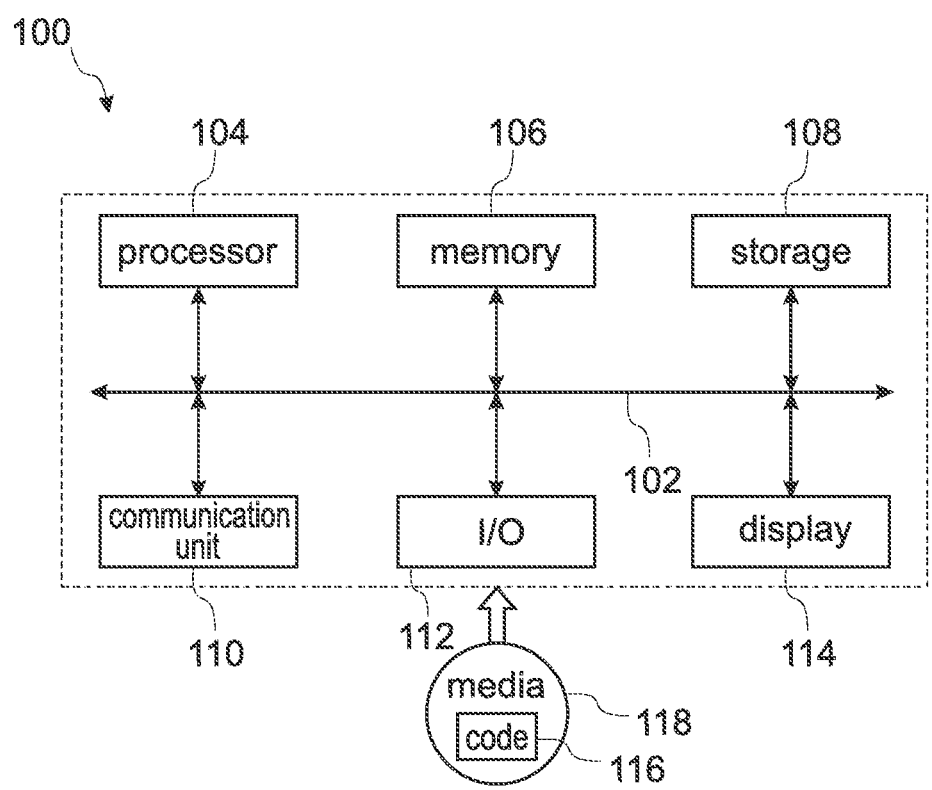
FIG. 1 is the illustration of an embodiment of a data processing system in which the computer usable program code of the computer program product in accordance with an embodiment of the present invention can be implemented.

FIG. 1 is the illustration of an embodiment of a data processing system 100 in which the computer usable program code of the computer program product in accordance with an embodiment of the present invention may be implemented.

The inverse treatment planning system 100 according to the invention comprises:
   at least a data bus system 102,
   a memory 106 coupled to the data bus system 102, wherein the memory comprises a computer usable program code, and
   a processing unit 104 coupled to the data bus system 102.

Figure 2:
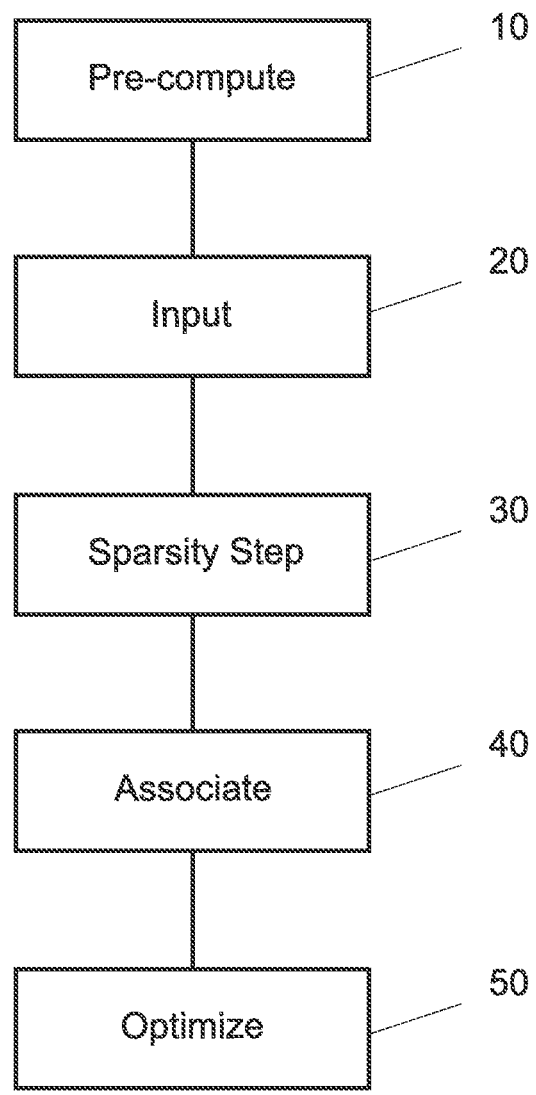
FIG. 2 shows a flow-chart representation of a method which can be implemented in an embodiment of the inverse treatment planning system according to the present invention.

FIG. 2 shows a flow-chart representation of a method which can be implemented in an embodiment of the inverse treatment planning system 100 according to the present invention.

Advantageously, the processing unit 102 is configured to execute the computer usable program code to
   pre-compute a dictionary composed of a list (or set) of possible dose shots' locations, sizes and shapes (step 10),
   define by the user the desired dose in the target area and potential additional constraints, for instance on the areas to be protected from too high dose radiation (step 20),
   solve a convex problem to determine the plan, i.e. to find which of those shots, and with which weights, will be actually used (steps 30, 40 and 50).

In one preferred embodiment, the set of pre-computed dose shots (step 10) can be located on a discrete three-dimensional (3D) grid of fixed resolution in a 3D space.

In one preferred embodiment, two consecutive locations on this grid in each of the three dimensions are spaced by a distance less than 1 mm, e.g. 0.5 mm.

As discussed, the first step of FIG. 1 (step 10) is to build a list dictionary of possible dose shots (or dose distributions patterns) located (centered) at all possible locations on a 3D grid, or a subset of them (e.g. those located only within the target area).

In one preferred embodiment, this step can be performed by considering pre-calculated patterns (so-called kernels) of individual dose distribution, of different sizes and shapes, and by translating them to all the considered grid points. This step can also be performed by taking into account the physical properties of the patient's head anatomy, based for instance on the medical images acquired for the planning.

The dictionary is thus the set of functions $$\{\alpha^j\}_{j=1}^N$$

with N denoting the size of the dictionary.

Each component $\alpha^j$ of the dictionary will be named "atom".

The complete dose distribution can be calculated as the weighted sum of the contributions from each atom. The dose d at any point (x, y, z) of the 3D space can be computed as $$d(x, y, z) = \sum_{j=1}^N s_j \alpha^j(x, y, z)$$

where $s_j$ denotes the weight associated to the j-th atom.

The objective of the inverse planning method is to find the minimum number of non-zero weights $s_j$ so that the constraints imposed by the user at step 20 are satisfied.

The complete dose distribution d can be calculated at a predefined number of points in the 3D space, for instance on a pre-defined grid G of P points.

This dose distribution d can be represented by a vector f of dimension P that can be defined as $$f = As$$

where A is an P×N matrix whose columns are the value of the dose delivered by each atom at each point of the grid G, and s is a vector of the weights of the atoms, of dimension N.

According to the invention, s has to be sparse, i.e. the number K of non-zero coefficients of s has to be much smaller than N. In a typical example, N may be as big as 100'000 or more, while K may be as small as 20 or less.

The positions of the non-zero elements in s determine which atoms in the dictionary will be used in the treatment, i.e. they determine the actual shot shapes and their locations. The values of s determine the shot weights.

Once building the dictionary A (step 10 in FIG. 2), a vector s with minimum number of non-zero elements is computed by satisfying the dose constraints defined by the user in step 20.

It must be understood that, even if the dose constraints in FIG. 2 are inputted by the user after the pre-computation of the dictionary, this inputting can be performed before the pre-computing step 10.

As optimization criteria, it is find a plan that minimizes a weighted L1 norm of vector s (i.e. the sum of the elements of the vector s) and meets all the dose constraints. The weighted L1 norm of s is closely related to the treatment time. This optimization problem can advantageously be formulated as a convex optimization problem (step 50), as only the weights of the individual dose shots are optimized (in fact simultaneously optimize the locations, sizes, shapes, and weights of the individual dose shots so as to guarantee a dose constraint will result in a non-convex optimization problem). In another embodiment, it is find a plan that minimizes a weighted L0 norm of vector s (i.e. the number of the elements of the vector s that are different from zero) and meets all the dose constraints. In another embodiment, it is find a plan that minimizes a weighted L2 norm of vector s and meets all the dose constraints.

Let T denote the set of indexes of the vector f corresponding to points that belong to the target region, let R denote those belonging to the sensitive areas to be protected, and Q the set of remaining indexes. Also, let $a_i$ denotes the i-th row of the matrix A. The i-th component of the vector f can be expressed as $$f_i = a_i s$$

i.e. the inner product of the i-th row of the dictionary A and the vector s. Thus, the optimal plan is computed by solving the following convex problem:

$$\min \|s\|_{1,w} \text{ such that } \begin{cases} a_i s \geq b_{min} & \forall i \in T \\ a_i s \leq b_{max} & \forall i \in R \\ a_i s \leq b_{min} & \forall i \in Q \\ s \geq 0 \end{cases}$$

where $$\|s\|_{1,w} = \sum_{i=1}^N w_i |s_i|$$

denotes the weighted L1 norm of the vector s with weights $w_i \geq 0$, $b_{min}$ is the minimum dose at the target region T, $b_{max}$ is the maximum allowed dose at sensitive regions R, and $s \geq 0$ denotes the positivity constraint on the values of s.

Additional constraints can be added at step 20 to the formulation as equality or inequality constraints. This can for instance be related to a desired dose gradient index.

The weighted L1 norm is a convex function that promotes sparse solutions, i.e. solving this constrained minimization problem will determine the sparsest vector s that meets all the dose constraints. The weights $w_i$ impose different penalties for the kernels in the dictionary. For example, if it is known a priori that a set of kernels take more time in the treatment, then the associated weights are larger than the rest. This will lead to an optimization problem that will minimize the treatment time. If no prior information is known about the delivery time, then all the weights can be set to one.

This optimization problem can then be solved by any convex optimization method, for instance by convex linear programming algorithms.

The inventive system proposes then an inverse treatment planning system wherein the complete dose distribution is modeled as a sparse linear combination of single shot dose chosen from a pre-computed dictionary or library of pre-computed single shot doses.

A convex constrained optimization procedure is used to determine the treatment plan. The shot weights are optimized, under sparsity constraint, to guarantee that the constraints on the dose distribution be met.

The optimization procedure does not require the user to provide initial shot locations, and the convex optimization formulation can include dose constraints applied both to the target region and to other areas such as sensitive structures to be protected against too high dose radiation.

FIG. 1 is an embodiment of a system 100 according to the invention. The system 100 of FIG. 1 may be located and/or otherwise operate at any node of a computer network, that may exemplarily comprise clients, servers, etc., and it is not illustrated in the figure. In the embodiment illustrated in FIG. 1, the system 100 includes communications fabric 102, which provides communications between processor unit 104, memory 106, persistent storage 108, communications unit 110, input/output (I/O) unit 112, and display 114.

Processor unit 104 serves to execute instructions for software that may be loaded into memory 106. Processor unit 104 may be a set of one or more processors or may be a multi-processor core, depending on the particular implementation. Further, processor unit 104 may be implemented using one or more heterogeneous processor systems in which a main processor is present with secondary processors on a single chip. As another illustrative example, the processor unit 104 may be a symmetric multi-processor system containing multiple processors of the same type.

In some embodiments, the memory 106 shown in FIG. 1 may be a random access memory or any other suitable volatile or non-volatile storage device. The persistent storage 108 may take various forms depending on the particular implementation. For example, the persistent storage 108 may contain one or more components or devices. The persistent storage 108 may be a hard drive, a flash memory, a rewritable optical disk, a rewritable magnetic tape, or some combination of the above. The media used by the persistent storage 108 also may be removable such as, but not limited to, a removable hard drive.

The communications unit 110 shown in FIG. 1 provides for communications with other data processing systems or devices. In these examples, communications unit 110 is a network interface card. Modems, cable modem and Ethernet cards are just a few of the currently available types of network interface adapters. Communications unit 110 may provide communications through the use of either or both physical and wireless communications links.

The input/output unit 112 shown in FIG. 1 enables input and output of data with other devices that may be connected to the system 100. In some embodiments, input/output unit 112 may provide a connection for user input through a keyboard and mouse. Further, input/output unit 112 may send output to a printer. Display 114 provides a mechanism to display information to a user.

Instructions for the operating system and applications or programs are located on the persistent storage 108. These instructions may be loaded into the memory 106 for execution by processor unit 104. The processes of the different embodiments may be performed by processor unit 104 using computer implemented instructions, which may be located in a memory, such as memory 106. These instructions are referred to as program code, computer usable program code, or computer readable program code that may be read and executed by a processor in processor unit 104. The program code in the different embodiments may be embodied on different physical or tangible computer readable media, such as memory 106 or persistent storage 108.

Program code 116 is located in a functional form on the computer readable media 118 that is selectively removable and may be loaded onto or transferred to the system 100 for execution by processor unit 104. Program code 116 and computer readable media 118 form a computer program product 120 in these examples. In one example, the computer readable media 118 may be in a tangible form, such as, for example, an optical or magnetic disc that is inserted or placed into a drive or other device that is part of persistent storage 108 for transfer onto a storage device, such as a hard drive that is part of persistent storage 108. In a tangible form, the computer readable media 118 also may take the form of a persistent storage, such as a hard drive, a thumb drive, or a flash memory that is connected to the system 100. The tangible form of computer readable media 118 is also referred to as computer recordable storage media. In some instances, computer readable media 118 may not be removable.

Alternatively, the program code 116 may be transferred to the system 100 from computer readable media 118 through a communications link to communications unit 110 and/or through a connection to input/output unit 112. The communications link and/or the connection may be physical or wireless in the illustrative examples. The computer readable media also may take the form of non-tangible media, such as communications links or wireless transmissions containing the program code.

The different components illustrated for data processing system 100 are not meant to provide architectural limitations to the manner in which different embodiments may be implemented. The different illustrative embodiments may be implemented in a data processing system including components in addition to or in place of those illustrated for data processing system 100. Other components shown in FIG. 1 can be varied from the illustrative examples shown. For example, a storage device in the system 100 is any hardware apparatus that may store data. Memory 106, persistent storage 108, and computer readable media 118 are examples of storage devices in a tangible form.

According to an embodiment, the system according to the invention is implemented on a processing unit (CPU) of a single computer. In another embodiment, it is implemented on a multi-cores computer, the cores working in parallel. In another embodiment, it is implemented on a Graphic Processing Unit (GPU) of a computer. In another embodiment, it is implemented on a plurality of computers, which work totally or partially in parallel.

According to an independent aspect of the invention, the system according to the invention can be shared in innovative training scenarios (including tele-training and remote coaching). In one embodiment, the interactive inverse planning is provided as a tele-service, the system running in a processing centre accessed by the users over secured Internet connections.

REFERENCE NUMBERS USED IN THE FIGURES

10 Pre-computing step
20 User inputting step (constraints)
30 Sparsity step
40 Association step
50 Optimization step
100 System
102 Data bus system
104 Processing unit
106 Memory
108 Persistent storage
110 Communication unit
112 I/O unit
114 Display
116 Program code
118 Computer readable media

The invention claimed is:

1. An inverse treatment planning system, comprising:
at least a data bus system,
a memory and a persistent storage coupled to the data bus system, wherein non-transitory instructions located on the persistent storage have been loaded into the memory,
a display coupled to the data bus system, wherein the display provides a mechanism to display information to a user, and
a processing unit coupled to the data bus system, wherein the processing unit is configured to execute said instructions to
pre-compute a set of individual beams, wherein the beam is comprised of a plurality of beamlets, each individual beam having a predetermined location inside and/or outside a target area, a size and a shape, associate a weight to each individual beam, based on at least one beam constraint or more beam constraints, so as to get individual weighted beams, wherein said processing unit executes said instructions to find the sparsest subset of said individual weighted beams, so as to satisfy said at least one beam constraint or more beam constraints creating thereby a beam distribution that can be produced by a machine, and wherein said display is coupled to the processing unit and is operable to output treatment parameters including for each individual weighted beam, its predetermined location, size and shape, provided by the processing unit.

2. The system of claim 1, wherein the processing unit executes the non-transitory instructions to find the minimum number of non-zero weights so as to satisfy said at least one beam constraint or more beam constraints.

3. The system of claim 1, wherein the number of non-zero weights is at least 1/100 of the number of pre-computed individual beams.

4. The system of claim 1, wherein the processing unit executes the non-transitory instructions to minimize a weighted L1 norm of the vector of weights while satisfying said at least one beam constraint or more beam constraints, so as to obtain an optimal subset of individual weighted beams.

5. The system of claim 1, wherein the processing unit executes the non-transitory instructions to minimize a weighted L0 norm of the vector of weights while satisfying said at least one beam constraint or more beam constraints, so as to obtain an optimal subset of individual weighted beams.

6. The system of claim 1, wherein the processing unit executes the non-transitory instructions to minimize a weighted L2 norm of the vector of weights while satisfying said at least one beam constraint or more beam constraints, so as to obtain an optimal subset of individual weighted beams.

7. The system of claim 1, wherein the processing unit executes the non-transitory instructions to locate each individual beams in a location of a three-dimensional grid.

8. The system of claim 1, wherein the processing unit is configured to execute the non-transitory instructions in real-time.

9. The system of claim 1, wherein said beam constraint comprises beam constraint applied to the target region and/or to other areas such as sensitive structures to be protected against too high beam radiation.

10. The system of claim 1, wherein the processing unit is configured to execute the non-transitory instructions to take into account the physical properties of the patient's head anatomy during the pre-computing of the set of individual beams.

11. The system of claim 1, wherein the processing unit executes the non-transitory instructions to apply a convex optimization criterion.

12. The system of the previous claim 11, said optimization criterion comprising minimizing a treatment time.

13. The system of claim 1, being a focal inverse treatment planning system.

14. The system of claim 13 being a radiation inverse treatment planning system.

15. The system of the previous claim 14, being a radiation inverse treatment planning system involving ionizing radiations.

16. A computer program product, comprising:

a tangible non-transitory computer usable medium including instructions for an inverse treatment planning, the instructions, when executed by a processor, cause the processor to:

pre-compute a set of individual beams, wherein the beam is comprised of a plurality of beamlets, each individual beam having a predetermined location inside and/or outside a target area, a size and a shape, associate a weight to each individual beam, based on at least one beam constraint or more beam constraints, so as to get individual weighted beams, wherein said processing unit executes the instructions to find the sparsest subset of said individual weighted beams so as to satisfy said at least one beam constraint or more beam constraints, and generate an output to control a display to output treatment parameters including fo each indidual weighted beam, its premdetermined location, size and shape, provided by the non-transitory computer usable medium.

17. A non-transitory computer data carrier storing presentation content created with an inverse treatment planning method, wherein, when said content is executed by a processor, causes the processor to perform the following steps:

pre-compute a set of individual beams, wherein the beam is comprised of a plurality of beamlets, each individual beam having a predetermined location inside and/or outside a target area, a size and a shape, associate a weight to each individual beam, based on at least one beam constraint or more beam constraints, so as to get individual weighted beams, wherein said processing unit executes the instructions to find the sparsest subset of said individual weighted beams so as to satisfy said at least one beam constraint or more beam constraints, and generate an output to control a display to output treatment parameters including for each individual weighted beam, its predetermined location, size and shape, provided by the non-transitory computer data carrier.

18. The system of claim 9, wherein said beam constraints are comprised in the following: beam distribution; locations, sizes and shapes of the individual beams; coverage, magnitude and gradients of the individual beams; a maximal treatment duration and a desired beam gradient index.

* * * * *